(12) United States Patent
Miller et al.

(10) Patent No.: US 7,432,305 B2
(45) Date of Patent: Oct. 7, 2008

(54) TAIL VARIANTS OF REDOX-ACTIVE THERAPEUTICS FOR TREATMENT OF MITOCHONDRIAL DISEASES AND OTHER CONDITIONS AND MODULATION OF ENERGY BIOMARKERS

(75) Inventors: Guy M. Miller, Carmel, CA (US); Sidney M. Hecht, Charlottesville, VA (US)

(73) Assignee: Edison Pharmaceuticals, Inc., San Jose, CA (US)

( * ) Notice: Subject to any disclaimer, the term of this patent is extended or adjusted under 35 U.S.C. 154(b) by 0 days.

(21) Appl. No.: 11/521,887

(22) Filed: Sep. 15, 2006

(65) Prior Publication Data

US 2007/0072943 A1    Mar. 29, 2007

Related U.S. Application Data

(60) Provisional application No. 60/717,678, filed on Sep. 15, 2005.

(51) Int. Cl.
  A61K 31/12   (2006.01)
  A61K 31/075  (2006.01)
  C07C 49/00   (2006.01)
  C07C 50/04   (2006.01)
  C07C 50/02   (2006.01)

(52) U.S. Cl. .............. 514/691; 514/718; 568/377; 568/731; 552/293; 552/309

(58) Field of Classification Search .............. None
See application file for complete search history.

(56) References Cited

U.S. PATENT DOCUMENTS

| | | | |
|---|---|---|---|
| 2,398,418 A | 4/1946 | Fieser | |
| 2,856,414 A | 10/1958 | Robeson et al. | |
| 3,071,512 A | 1/1963 | Feldmann | |
| 3,406,188 A | 10/1968 | Fletcher | |
| 3,705,239 A | 12/1972 | Gregory | |
| 3,849,453 A | 11/1974 | Morrimoto et al. | |
| 3,896,153 A | 7/1975 | Sato et al. | |
| 3,909,376 A | 9/1975 | Degner | |
| 3,957,836 A | 5/1976 | Morimoto et al. | |
| 4,127,608 A | 11/1978 | Olson et al. | |
| 4,153,614 A | 5/1979 | Barner et al. | |
| 4,185,154 A | 1/1980 | Olson et al. | |
| 4,201,726 A | 5/1980 | Olson et al. | |
| 4,201,879 A | 5/1980 | Barner et al. | |
| 4,234,490 A | 11/1980 | Barner et al. | |
| 4,243,598 A | 1/1981 | Olson et al. | |
| 4,310,465 A * | 1/1982 | Olson et al. ............ 552/310 |
| 4,388,312 A | 6/1983 | Terao et al. | |
| 4,393,075 A * | 7/1983 | Terao et al. ............ 514/519 |
| 4,436,753 A | 3/1984 | Imada et al. | |
| 4,491,594 A * | 1/1985 | Ogawa et al. ........... 514/690 |
| 4,495,104 A | 1/1985 | Imada et al. | |
| 4,559,177 A | 12/1985 | Okutani et al. | |
| 4,592,867 A | 6/1986 | Yu et al. | |
| 4,599,232 A | 7/1986 | Bertelli | |
| 4,694,090 A | 9/1987 | Shiono et al. | |
| 4,814,346 A | 3/1989 | Albert et al. | |
| 4,818,441 A | 4/1989 | Imada et al. | |
| 4,831,265 A | 5/1989 | Watanabe et al. | |
| 5,057,514 A | 10/1991 | Tatsuoka et al. | |
| 5,059,627 A | 10/1991 | Goto et al. | |
| 5,179,092 A | 1/1993 | Tatsuoka et al. | |
| 5,180,742 A | 1/1993 | Terao et al. | |
| 5,210,239 A | 5/1993 | Abe et al. | |
| 5,229,385 A * | 7/1993 | Terao et al. ............ 514/235.5 |
| 5,288,752 A | 2/1994 | Tatsuoka et al. | |
| 5,292,768 A | 3/1994 | Tatsuoka et al. | |
| 5,304,658 A | 4/1994 | Terao et al. | |
| 5,547,827 A | 8/1996 | Chen et al. | |
| 5,600,029 A | 2/1997 | Kaneko et al. | |
| 5,846,988 A | 12/1998 | Hellberg | |
| 5,969,133 A | 10/1999 | Ono et al. | |
| 5,981,601 A | 11/1999 | Nagley et al. | |
| 6,011,046 A | 1/2000 | Ohkawa et al. | |
| 6,045,826 A | 4/2000 | Borowy-Borowski et al. | |
| 6,083,982 A | 7/2000 | Wechter et al. | |
| 6,133,278 A | 10/2000 | Terao et al. | |
| 6,133,322 A | 10/2000 | Rustin et al. | |

(Continued)

FOREIGN PATENT DOCUMENTS

DE    38 18 696 C1    3/1989

(Continued)

OTHER PUBLICATIONS

Cressman et al. One-Step Synthesis of Polyalkyl-2-iodo-p-benzoquinones. Journal of Organic Chemistry, 1966, 31 (4), p. 1279-1281.*

(Continued)

*Primary Examiner*—Sikarl A. Witherspoon
(74) *Attorney, Agent, or Firm*—Morrison & Foerster LLP

(57) ABSTRACT

Methods of treating or suppressing mitochondrial diseases, such as Friedreich's ataxia (FRDA), Leber's Hereditary Optic Neuropathy (LHON), mitochondrial myopathy, encephalopathy, lactacidosis, stroke (MELAS), or Kearns-Sayre Syndrome (KSS) are disclosed, as well as compounds useful in the methods of the invention. Energy biomarkers useful in assessing the metabolic state of a subject and the efficacy of treatment are also disclosed.

21 Claims, No Drawings

U.S. PATENT DOCUMENTS

| | | | |
|---|---|---|---|
| 6,136,859 | A | 10/2000 | Henriksen |
| 6,150,402 | A | 11/2000 | Wechter et al. |
| 6,271,266 | B1 | 8/2001 | Miyamoto et al. |
| 6,300,377 | B1 | 10/2001 | Chopra |
| 6,331,532 | B1 | 12/2001 | Murphy et al. |
| 6,342,516 | B1 | 1/2002 | Umeda et al. |
| 6,417,233 | B1 * | 7/2002 | Sears et al. ............... 514/549 |
| 6,426,362 | B1 | 7/2002 | Miller et al. |
| 6,433,199 | B1 | 8/2002 | Ono et al. |
| 6,454,184 | B1 | 9/2002 | Merkel et al. |
| 6,740,338 | B1 | 5/2004 | Chopra |
| 6,764,768 | B2 | 7/2004 | Mrksich et al. |
| 6,852,895 | B2 | 2/2005 | Lipshutz et al. |
| 6,977,270 | B2 | 12/2005 | Baldenius et al. |
| 2002/0182196 | A1 | 12/2002 | McCleary |
| 2003/0119054 | A1 | 6/2003 | Mrksich et al. |
| 2004/0043103 | A1 | 3/2004 | McCLeary |
| 2004/0156871 | A1 | 8/2004 | Borowy-Borowski et al. |
| 2005/0043553 | A1 | 2/2005 | Smith et al. |
| 2005/0065099 | A1 | 3/2005 | Walkinshaw et al. |
| 2005/0065150 | A1 | 3/2005 | Wang et al. |
| 2005/0186518 | A1 | 8/2005 | Masskasky et eal. |
| 2005/0222218 | A1 | 10/2005 | Meier et al. |
| 2006/0002885 | A1 | 1/2006 | Mielke et al. |
| 2006/0281809 | A1 | 12/2006 | Miller et al. |

FOREIGN PATENT DOCUMENTS

| | | |
|---|---|---|
| EP | 0 134 198 A1 | 3/1985 |
| EP | 0 619 313 A1 | 10/1994 |
| EP | 0 719 552 A2 | 12/1995 |
| EP | 0 719 552 A3 | 12/1995 |
| EP | 1 378 753 A1 | 1/2004 |
| EP | 1 378 753 B1 | 1/2004 |
| FR | 1.201.200 | 12/1959 |
| FR | 75.631 | 6/1961 |
| FR | 5.531 M | 12/1967 |
| FR | 1.536.576 | 8/1968 |
| JP | 40-9029 | 5/1965 |
| JP | 56-140943 A | 11/1981 |
| JP | 57-050935 A | 3/1982 |
| JP | 58-083698 A | 5/1983 |
| JP | 58-193689 A | 11/1983 |
| JP | 60-28919 A | 2/1985 |
| JP | 61-040236 A | 2/1986 |
| JP | 1-093554 A | 4/1989 |
| JP | 1 209445 A | 8/1989 |
| JP | 5-11467 A | 1/1993 |
| JP | 8-92151 A | 4/1996 |
| JP | 2000-202297 A | 7/2000 |
| JP | 2003-64017 A | 3/2003 |
| JP | 2003-137716 A | 5/2003 |
| WO | WO-93/24650 A1 | 12/1993 |
| WO | WO-98/34646 A2 | 8/1998 |
| WO | WO-00/50043 A1 | 8/2000 |
| WO | WO-01/52822 A1 | 7/2001 |
| WO | WO-01/92215 A2 | 12/2001 |
| WO | WO-01/92215 A3 | 12/2001 |
| WO | WO-02/34259 A1 | 5/2002 |
| WO | WO-02/067864 A2 | 9/2002 |
| WO | WO-02/067864 A3 | 9/2002 |
| WO | WO-2004/003565 A2 | 1/2004 |
| WO | WO-2004/003565 A3 | 1/2004 |
| WO | WO-2004/042353 A2 | 5/2004 |
| WO | WO-2004/042353 A3 | 5/2004 |
| WO | WO-2005/000357 A2 | 1/2005 |
| WO | WO-2005/000357 A3 | 1/2005 |
| WO | WO-2005/019232 A1 | 3/2005 |
| WO | WO-2005/033092 A1 | 4/2005 |
| WO | WO-2005/033093 A1 | 4/2005 |
| WO | WO-2005032544 A1 | 4/2005 |
| WO | WO-2005/105159 A2 | 11/2005 |
| WO | WO-2005/105159 A3 | 11/2005 |
| WO | WO-2006/130775 A2 | 12/2006 |
| WO | WO-2006/130775 A3 | 12/2006 |
| WO | WO-2007/035496 A1 | 3/2007 |
| WO | WO-2007/095630 A2 | 8/2007 |
| WO | WO-2007/095630 A3 | 8/2007 |

OTHER PUBLICATIONS

Shi et al. Hydrophobic Acceleration of Electron Transfer Processes. Journal of Organic Chemistry, 1996, vol. 61, p. 4698-4702.*

Gu et al. Synthesis and Inhibitory Activity of Bromoquinone Derivatives. Tetrahedron, 1990, 46 (9), pp. 3199-3210.*

Adelwöhrer, C. et al. (2005, e-pub. Aug. 2, 2005). "Novel Tocopheryl Compounds XX. 1,3,8-Trioxaphenanthrenes Derived from γ-Tocopherol," *Tetrahedron* 61:9070-9074.

Armstrong, J.S. et al. (Dec. 5, 2003). "The Coenzyme $Q_{10}$ Analog Decylubiquinone Inhibits the Redox-Actived Mitochondrial Permeability Transition," *The Journal of Biological Chemistry* 278(49):49079-49084.

Asgill, J.O. et al. (Jan. 4, 1978). "Chromenylation of 2-Napthol and Alkylhydroquinones: Short Synthesis of (2RS,4'R, 8'R)-α-Tocopherol (Vitamin E) and (2RS,4'R, 8'R)-β-Tocopherol," *The Journal of The Chemical Society Chemical Communications* 1:59-60.

Boyer, P.D. (Feb. 19, 1951). "The Preparation of Reversible Oxidation Product of α-Tocopherol, α-Tocoperoxide and of Related Oxides," *Journal of the American Chemical Society* 73(2):733-740.

Briere, J-J. et al. (Apr. 16, 2004). "Wuinone Analogues Regulate Mitochondrial Substrate Competitive Oxidation," *Biochemical and Biophysical Research Communications* 316(4):1138-1142.

Calviello, G. et al. (2003). "γ-Tocopheryl Wuinone Inducs Apoptosis in Cancer Cells Via Caspase-9 Activation and Cytochrome *c* Release," *Carcinogenesis* 24(3):427-433.

Caplus Accession No. 1967:18647, created May 12, 1984, 9 pages.
Caplus Accession No. 1969:433438, created May 12, 1984, 1 page.
Caplus Accession No. 169:524242, created May 12, 1984, 3 pages.
Caplus Accession No. 1989:553350, created Oct. 28, 1999, 4 pages.
Caplus Accession No. 2003:166979, created Mar. 5, 2003, 5 pages.
Caplus Accession No. 2003:487787, created Jun. 27, 2003, 8 pages.

Cohen, N. et al. (1981). "Studies on the Total Synthesis of (2R,4'R,8'R)-α-Tocopherol (Vitamin E). Stereospecific Cyclizations Leading to Optically Active Chromans," *The Journal of Organic Chemistry* 46(12):2445-2450.

Dowd, P. et al. (Aug. 1995). "On the Mechanism of the Anticlotting Action of Vitamin E Quinone," *Proceedings of The National Academy of Science USA* 92:8171-8175.

Dürckheimer, W. et al. (Oct 20, 1964). "The Chemistry of 9-Hydroxy-α-Tocopherone, A Quinone Hemiacetal," *Journal of The American Chemical Society* 86(20):4388-4393.

Echtay, K.S. et al. (Nov. 30, 2000). "Coenzyme Q is an Obligatory Cofactor for Uncoupling Protein Function," *Nature* 408:609-613.

Fujishima, T. et al. (1996, e-pub. Sep. 23, 2006). "Synthesis of Vitamin E Analogues: Possible Active Forms of Vitamin E," *Arch. Pharm. Pharma. Med. Chem.* 329(1):27-34.

Gille, L. et al. (2001). "Effects of Tocopheryl Quinone on the Heart: Model Experiments with Xanthine Oxidase, Heart Mitochondria, and Isolted Perfused Rat Hearts," *Free Radical Biology and Medicine* 30(8):865-876.

Gille, L. et al. (2004). "Oxidized Vitamin E and Ubiquinone: Competition for Binding Sited of the Mitochondrial Cytochrome $bc_1$ Complex?" *Annals of the New York Academy of Sciences* 1031:341-343.

Gille, L. et al. (2004). "Redox-Interaction of a α-Tocopheryl Quinone with Isolated Mitochondrial Cytochrome $bc_1$ Complex," *Biochemical Pharmacolgy* 68:373-381.

Goodhue, C.T. et al. (May 1965). "Reactions of Vitamin E with Peroxides. II. Reaction of Benzoyl Peroxide with *d*α-Tocopherol in Alcohols," *Biochemistry* 4(5):854-858.

Green, J. et al. (1966) "Bond Stabilisation in Tocopherols. Part I. The Claisen Rearrangement of Allyl Tocopheryl Ethers," *Journal of the Chemical Society C*, pp. 1422-1427.

Hagio, K. et al. (Apr. 1974). "Synthesis and Reactions of 4-Dimethylsulfuranylidene-2,3,-Dioxotetrahydrofuran Derivatives," *Bulletin of the Chemical Society of Japan* 47(4):909-916.

Infante, J.P. (1999). "A Function for the Vitamin E Metabolite α-Tocopherol Quinone as an Essential Enzyme Cofactor for the Mitochondrial Fatty Acid Desatures," *The FEBS Letters* 446:1-5.

Inoue, S. et al. (1987). "Improved General Method of Ortho Alkylation of Phenols Using Alkyl Isopropyl Sulfide, Sulfryl Chloride, and Triethylamine. An Expedient Synthesis of Representative Oxygen Heterocycles and (2R,4'R, 8'R)-α-Tocopherol," *Journal of Organic Chemistry* 52:5495-5497.

James, A.M. et al. (Jun. 3, 2005). "Interactions of Mitochondria-Targeted and Untargeted Ubiquinones with the Mitochondrial Respiratory Chain and Reactive Oxygen Species," *The Journal of Biological Chemistry* 280(22):21295-21312.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (Oct. 23, e-pub. Aug. 15, 2003). "Mitochondria-Targeted Antioxidants Protect Friedrich Ataxia Fibroblasts from Endogenous Oxidative Stress more Effectively than Untargeted Antioxidants," *The FASEB Jornal* 17(13):1972-1974.

Kelso, G.F. et al. (Feb. 16, 2001)"Selective Targeting of a REdox-Active Ubiquinone to Mitochondria Within Cells," *The Jornal of Biological Chemistry* 276(7):4588-4596.

Kumadaki, I. et al. (1989). "Trifluoromethylation of Tocopherols," *Synthetic Communications* 19(1&2):173-177.

Larisch, B. et al. (Jul. 1996). "Reactions of Dehydroascorbic Acid with Primary Aliphatic Amines Including $N^\alpha$-Acetyllysine, "*Journal of Agricultural and Food Chemistry* 44(7):1630-1634.

Lenaz, G. et al. (2000). "Mitochondrial Bioenergetics in Aging," *Biochimica et Biophysica Acta* 1459:397-404.

Lipshutz, B.H. et al. (Feb. 12, 1998). "An Expeditious Route to $CoQ_n$, Vitamins $K_1$ and $K_2$, and Related Allytated *para*-Quinones Utilizing Ni(0) Catalysis," *Tetrahedron* 54(7):1241-1253.

Mackenzie, J.B. et al. (1950). "The Biological Activity of α-Tocopherylhydroquinone and α-Tocopherylquinone," *Journal of Biological Chemistry* 183(2):655-662.

Maloney, D.J. et al. (2005, e-pub. Aug. 20, 2005). "A Stereocontrolled Synthesis of δ-*trans*-Tocotrienoloic Acid," *Acid Letters* 7(19):4297-4300.

Marpat Accession No. 138:187513, 2 pages.

Mazzini, F. et al. (2005, e-pub. Nov. 30, 2004). "Easy Route to Lebeled and Unlabeled *R, R, R,*-γ-Tocopherol by Aryl Demethylation of α-Homologues," *Tetrahedron* 61:813-817.

Mukai, K. et al. (1989). "Synthesis and Kinetic Study of Antioxidant Activity of New Tocopherol (Vitamin E) Compounds," *The Journal of Organic Chemistry* 54(3):552-556.

Mukai, K. et al. (1989). "Synthesis and Stopped-Flow Investigation of Antioxidant Activity of Tocopherols. Finding of New Tocopherol Derivatives Having the Highest Antioxidant Activity Among Phenolic Antioxidants," *The Journal of Organic Chemistry* 54(3):557-560.

Mukai, K. et al. (19910. "Structure-Activity Relationship in the Quenching Reaction of Singlet Oxygen by Tocopherol (Vitamin E) Derivatives and Related Phenols. Finding of Linear Correlation Between the Rates of Quenching of Singlet Oxygen and Scavenging of Peroxyl and Phenoxyl Radicals in Solution," *The Journal of Organic Chemistry* 56(13):4188-4192.

Omura, K. (1989). "Iodine Oxidation of α-Tocopherol and Its Model Compound in Alkaline Methanol: Unexpected Isomerization of the Product Quinone Monoketals," *The Journal of Organic Chemistry* 54(8):1987-1990.

Pelter, A. et al. (1997). "The Synthesis of 82-Methoxy-2*H*, 6*H*-Chromen-6-ones and Corresponding 2*H*-Chromenes by a Unique Process Utilising Phenolic Oxidation," *Tetrahedron* (53(11):3879-3916.

Siegel, D. et al. (1997). "The Reduction of α-Tocopherolquinone by Human NAD(P)H: Quinone Oxidoreductase: The Role of α-Tocopherolhydroquinone as a Cellular Antioxidant," *Molecular Pharmacology* 53:300-305.

Staniek, K. et al. (Nov. 1, 2005). "The Protection of Bioenergetic Functions in Mitochondria by New Synthetic Chromanols," *Biochemical Pharmacology* 70(9):1361-1370.

Vatassery, G. et al. (Apr. 5, 2004). "Iron Uncouples Oxidative Phosphorylation in Brain Mitochondria Isolated From Vitamin E-Deficient Rats," Biochimica et Biophysica Acta 1688(3):265-273.

Weichet, J. et al. (1996). "Vitamin K and Vitamin E Series. XVIII. Synthesis of New Analogs of Vitamin E and Their Derivatives," *Collection of Czeckoslov. Chem. Commun.* 31:4598-4609.

Zheng, A. et al. (1999). "A Redox-Sensitive Resin Linker for the Solid Phase Synthesis of *C*-Terminal Modified Peptides," *Journal of Organic Chemistry* 64:156-161.

Zwaiyed, F.R. et al. (2003). "Vitamin E and its Derivative Antihypoxic Effectivity in Rats Under Modeling of Hypoxic Conditions of Different Origin," Ukrainskii Biokhimicheskii Zhurnal 75(2):67-71.

Trumpower, B.L. (Jul. 15, 1990). "The Protonmotive Q Cycle. Energy Transduction by Coupling of Proton Translocation to Electron Transfer by Cytochrome $bc_1$ Complex," *The Journal of Biological Chemistry* 265(20):11409-11412.

Asin-Cayuela, J. et al. (Jul. 30, 2004). "Fine-Tuning the Hydrophobicity of a Mitochondria-Targeted Antioxidant," *FEBS Letters* 571(1-3):9-16.

Babiroli, B. et al. (Jul. 1995). "Lipoic (Thioctic) Acid Increases Brain Energy Availability and Skeletal Muscle Performance as Shown by In Vivo $^{31}$P-MRS in a Patient with Mitochondrial Cytopathy," *Journal of Neurology* 242(7):472-477.

Chariot, P. et al. (Apr. 1994). "Determination of the Blood Lactase : Pyruvate Ratio as a Noninvasive Test for the Diagnosis of Zidovudine Myopathy," *Arthritis & Rheumatism* 37(4):583-586.

Chariot, P. et al. (Jul. 1994). "Optimal Handling of Blood Samples for Routine Measurement of Lactate and Pyruvate," *Archives of Pathology & Laboratory Medicine* 118(7):695-697.

Erhola, M. et al. (Jun. 9, 1997). "Biomaker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.

Fabrizi, G.M. et al. (Apr. 1996). "Autosomal Dominant Limb Girdle Myopathy with Ragged-Red Fibers and Cardiomyopathy: A Pedigree Study by In Vivo $^{31}$P-MR Spectroscopy Indicating a Multisystem Mitochondrial Defect," *Jornal of the Neurological Sciences* 137(1):20-27.

Fieser, L.F. et al. (Sep. 1942). "Alkylation of Para Quinones with Acyl Peroxides," *Journal of the American Chemical Society* 64(9):2060-2065.

Gu, L-Q. et al. (1990). "Effect of Substituents of the Benzoquinone Ring on Electron-Transfer Activities of Ubiquinone Derivatives," *Biochimica et Biophysica Acta* 1015(3):482-492.

Honda, M. et al. (Jun. 2000). "Correlation of Urinary 8-Hydroxy-2'-Deoxyguanosine (8-OHdG), a Biomaker of Oxidative DNA Damage, and Clinical Features of Hematological Disorders: A Pilot Study," *Leukemia Research* 24(6):461-468.

Hübscher, J.V. et al. (1990). "Total Synthesis of Naturally Occurring α - Tocopherol. Asymmetric Alkylation and Asymmetric Epoxidation as Means to Introduce (*R*)-Configuration at C(2) of the Chroman Moiety," *Helvetica Chimica Acta* 73(4-6):1068-1086 (English Translation of Abstracts Only).

International Search Report mailed on Feb. 8, 2007, for PCT Patent Application No. PCT/US2006/036052 filed on Sep. 15, 2006, 9 pages.

Kaufman, P. et al. (Apr. 27, 2004). "Cerebral Lactic Acidosis Correlates with Neurological Impairment in MELAS," *Neurology* 62(8):1297-1302.

Kim, J.Y. et al. (May 2004). "Urinary 8-Hydroxy-2'-Deoxyguanosine as a Biomaker of Oxidative DNA Damage in Workers Exposed to Fine Particulates," *Environmental Health Perspectives* 112(6):666-671.

Lynch, D.R. et al. (May 2002). "Near Infrared Muscle Spectroscopy in Patients with Friedreich's Ataxia," *Muscle& Nerve* 25(5):664-673.

Matthews, P.M. et al. (Apr. 1991). "In Vivo Magnetics Resonance Spectroscopy on Brain and Muscle in a Type of Mitochondrial Encephalomyopathy (MERRF)," *Annals of Neurology* 29(4):435-438.

Monte, W. T. et al. (May/Jun. 2001). "An Efficient Process for the Synthesis of γ-Arylbutanals via Copper-Mediated Grignard Coupling," *Organic Process Research & Development* 5(3):267-269.

Munnich, A. et al. (1992). "Clinical Aspects of Mitochondrial Disorders," *Journal of Inherited Metabolic Disease* 15(4):448-455.

Pelter, A. et al. (1993). "Phenolic Oxidations with Phenyliodonium Diacetate," *Journal of the Chemical Society, Perkins Transactions 1* 16:1891-1896.

Pileni, M.P. et al. (1980). "Zinc Porphyrin Sensitized Reduction of Simple and Functional Quinones in Micellar Systems," *Journal of Physical Chemistry* 84(14):1822-1825.

Pilger, A. et al. (Sep. 2001). "Longitudinal Study of Urinary 8-Hydroxy-2'-Deoxyguanosine Excretion in Healthy Adults," *Free Radical Research* 35(3):273-280.

Piña, I.L. et al. (Mar. 4, 2003). "Exercise and Heart Failure: A Statement From the American Heart ASsociation Committee on Exercise, Rehabilitation, and Prevention," *Circulation* 107(8):1210-1225.

Rolfe, P. (2000). "In Vivo Near-Infrared Spectroscopy," *Annual Review of Biomedical. Engineering* 2:715-754.

Shiraishi, M. et al. (Sep. 1989). "Quinones. 4. Novel Eicosanoid Antagonists: Synthesis and Pharmacological Evaluation," *Journal of Medicinal Chemistry* 32(9):2214-2221.

Silbert, L.S. et al. (Jun. 2, 1959). "Peroxides. VI. Preparation of *t*-Butyl Peresters and Diacyl Peroxides of Aliphatic Monobasic Acids," *Journal of the American Chemical Society* 81(10): 2364-2367.

STN Accession No. 1985:621368, last visited Jan. 23, 2007, 1 page.

STN Accession No. 1992:58878, last visited Jan. 23, 2007, 1 page.

STN Accession No. 1993;21870, last visited Jan. 23, 2007, 2 pags.

Strangman, G. et al. (Oct. 1, 2002). "Non-Invasive Neuroimaging Using Near-infrared Light," *Biological Psychiatry* 52(7):679-693.

Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Annals of Neurology*, 51(1):38-44.

Taivassalo, T. et al. (Feb. 2003). "The Spectrum of Exercise Tolerance in Mitochondrial Myopathies: A Study of 40 Patients," *Brain* 126(Pt2)413-423.

Thomas, A.D. et al. (Aug. 8, 1986). "Repetitive Diels-Alder Reactions for the Growth of Linear Polyacenequinoid Derivatives," *Journal of Organic Chemistry* 51(22):4160-4169.

Ueda, K. et al. (Feb. 1997). "Evaluation of Changes in Hepatic Energy Metabolism during Exercise by Ketone Body Ration in Humans," *Journal of Cardiology* 29(2):95-102 (English Translation of Abstract Only).

Van Beekvelt, M.C.P. et al. (Oct. 1999). "Quantivative Near-Infared Spectroscopy Discriminates Between Mitochondrial Myopathies and Normal Muscle," *Annals of Neurology* 46(4):667-670.

Written Opinion mailed on Feb 8, 2007, for PCT Patent Application No. PCT/US2006/036052 filed on Sep. 15, 2006, 11 pages.

\* cited by examiner

TAIL VARIANTS OF REDOX-ACTIVE THERAPEUTICS FOR TREATMENT OF MITOCHONDRIAL DISEASES AND OTHER CONDITIONS AND MODULATION OF ENERGY BIOMARKERS

CROSS REFERENCE TO RELATED APPLICATIONS

This application claims the priority benefit of U.S. Provisional Patent Application No. 60/717,678, filed Sep. 15, 2005. The entire content of that application is hereby incorporated herein by reference in its entirety.

TECHNICAL FIELD

The application discloses compositions and methods useful for treatment or suppression of diseases due to mitochondrial disorders, such as Friedreich's ataxia, Leber's Hereditary Optic Neuropathy, Kearns-Sayre Syndrome, and mitochondrial myopathy, encephalopathy, lactacidosis, stroke (MELAS), and for modulating energy biomarkers in a subject.

BACKGROUND

Mitochondria are organelles in eukaryotic cells, popularly referred to as the "powerhouse" of the cell. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Kreb's cycle), which generates reduced nicotinamide adenine dinucleotide (NADH+$H^+$) from oxidized nicotinamide adenine dinucleotide (NAD$^+$), and oxidative phosphorylation, during which NADH+$H^+$ is oxidized back to NAD$^+$. (The citric acid cycle also reduces flavin adenine dinucleotide, or FAD, to $FADH_2$; $FADH_2$ also participates in oxidative phosphorylation.)

The electrons released by oxidation of NADH+$H^+$ are shuttled down a series of protein complexes (Complex I, Complex II, Complex III, and Complex IV) known as the respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The citric acid cycle and oxidative phosphorylation are preceded by glycolysis, in which a molecule of glucose is broken down into two molecules of pyruvate, with net generation of two molecules of ATP per molecule of glucose. The pyruvate molecules then enter the mitochondria, where they are completely oxidized to $CO_2$ and $H_2O$ via oxidative phosphorylation (the overall process is known as aerobic respiration). The complete oxidation of the two pyruvate molecules to carbon dioxide and water yields about at least 28-29 molecules of ATP, in addition to the 2 molecules of ATP generated by transforming glucose into two pyruvate molecules. If oxygen is not available, the pyruvate molecule does not enter the mitochondria, but rather is converted to lactate, in the process of anaerobic respiration.

The overall net yield per molecule of glucose is thus approximately at least 30-31 ATP molecules. ATP is used to power, directly or indirectly, almost every other biochemical reaction in the cell. Thus, the extra (approximately) at least 28 or 29 molecules of ATP contributed by oxidative phosphorylation during aerobic respiration are critical to the proper functioning of the cell. Lack of oxygen prevents aerobic respiration and will result in eventual death of almost all aerobic organisms; a few organisms, such as yeast, are able to survive using either aerobic or anaerobic respiration.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Genetic defects in the proteins making up the respiratory chain lead to severe disease states. One such disease is Friedreich's ataxia (FRDA or FA). Friedreich's ataxia is an autosomal recessive neurodegenerative and cardiodegenerative disorder caused by decreased levels of the protein frataxin. Frataxin is important for the assembly of iron-sulfur clusters in mitochondrial respiratory-chain complexes. Estimates of the prevalence of FRDA in the United States range from 1 in every 22,000 people (see World-Wide-Web address .nlm.nih.gov/medlineplus/ency/article/001411.htm) to I in 50,000 people (World-Wide-Web address .umc-cares.org/health_info/ADAM/Articles/001411.asp). The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Another disease linked to mitochondrial dysfunction is Leber's Hereditary Optic Neuropathy (LHON). The disease is characterized by blindness which occurs on average between 27 and 34 years of age (World-Wide-Web address .ncbi.nlm.nih.gov/entrez/dispomim.cgi?id=535000); blindness can develop in both eyes simultaneously, or sequentially (one eye will develop blindness, followed by the other eye two months later on average). Other symptoms may also occur, such as cardiac abnormalities and neurological complications.

Yet another devastating syndrome resulting from mitochondrial defects is mitochondrial myopathy, encephalopathy, lactacidosis, and stroke (MELAS). The disease can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke. Other severe complications, including neurological symptoms, are often present, and elevated levels of lactic acid in the blood occur.

Another mitochondrial disease is Kearns-Sayre Syndrome (KSS). KSS is characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis. Thus, KSS may affect many organ systems.

The four diseases above appear to be caused by defects in complex I of the respiratory chain. Electron transfer from complex I to the remainder of the respiratory chain is mediated by the compound coenzyme Q (also known as ubiquinone). Oxidized coenzyme Q ($CoQ^{ox}$ or ubiquinone) is reduced by complex I to reduced coenzyme Q ($CoQ^{red}$ or ubiquinol). The reduced coenzyme Q then transfers its electrons to complex III of the respiratory chain (skipping over complex II), where it is re-oxidized to $CoQ^{ox}$ (ubiquinone). $CoQ^{ox}$ can then participate in further iterations of electron transfer.

Very few treatments are available for patients suffering from these diseases. Recently, the compound idebenone has been proposed for treatment of Friedreich's ataxia. While the clinical effects of idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Patent Application Publication No. 2005/0043553); clinical results for MitoQ have not yet been reported. For KSS, administration of coenzyme Q10 (CoQ10) and vitamin supplements have shown only transient beneficial effects in individual cases.

Accordingly, there is a serious and unmet need for effective treatments of mitochondrial disorders, such as Friedreich's ataxia, Leber's hereditary optic neuropathy, MELAS, and Kearns-Sayre Syndrome.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

DISCLOSURE OF THE INVENTION

In one embodiment, the compounds are selected from the group of formula I consisting of:

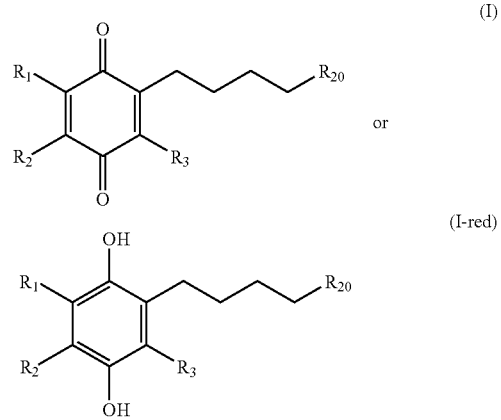

where $R_1$, $R_2$, and $R_3$ are independently selected from —$C_1$-$C_4$ alkyl, —$C_1$-$C_4$ haloalkyl, —CN, —F, —Cl, —Br, and —I; and $R_{20}$ is independently selected from —$C_1$-$C_{20}$ alkyl, —$C_1$-$C_{20}$ alkenyl, —$C_1$-$C_{20}$ alkynyl, and —$C_1$-$C_{20}$ containing at least one double bond and at least one triple bond; and all salts, stereoisomers, mixtures of stereoisomers, prodrugs, metabolites, solvates, and hydrates thereof. All $R_1$, $R_2$, and $R_3$ groups may be linear, branched, or cyclic. $R_{20}$ groups may be linear or branched. $C_1$-$C_{20}$ alkenyl contains at least one double bond. $C_1$-$C_{20}$ alkynyl contains at least one triple bond.

In one embodiment of the above-recited compounds of formula I, the proviso is added that $R_{20}$ cannot be $C_6$ n-alkyl, $C_7$ n-alkyl, or $C_{11}$ n-alkyl. In another embodiment of the above-recited compounds of formula I, the proviso is added when $R_1$, $R_2$, and $R_3$ are all methyl, $R_{20}$ cannot be $C_6$ n-alkyl, $C_7$ n-alkyl, or $C_{11}$ n-alkyl. In another embodiment of the above-recited compounds of formula I, the proviso is added that $R_{20}$ excludes $C_6$ n-alkyl when $R_3$ is bromo, one of $R_1$ and $R_2$ is methyl, and the other one of $R_1$ and $R_2$ is bromo. Any one, any two, or all three of these provisos can also be added to any embodiment of formula I described herein.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula I as described above.

In another embodiment, the invention embraces compounds of formula I where $R_1$, $R_2$, and $R_3$ are independently selected from —$C_1$-$C_4$ alkyl, —$C_1$-$C_4$ haloalkyl, —CN, —F, —Cl, —Br, and —I, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula I, where $R_1$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula I where $R_1$, $R_2$, and $R_3$ are independently selected from methyl, ethyl, n-propyl, and n-butyl, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula I where $R_1$, $R_2$, and $R_3$ are independently selected from $C_2$-$C_4$ alkyl; and all salts, stereoisomers, mixtures of stereoisomers, prodrugs, metabolites, solvates, and hydrates thereof.

In another embodiment, the invention embraces compounds of formula I where $R_1$, $R_2$, and $R_3$ are independently selected from $C_2$-$C_4$ n-alkyl; and all salts, stereoisomers, mixtures of stereoisomers, prodrugs, metabolites, solvates, and hydrates thereof.

In another embodiment, the invention embraces compounds of formula I, where $R_1$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; and all salts, stereoisomers, mixtures of stereoisomers, prodrugs, metabolites, solvates, and hydrates thereof.

In another embodiment, the invention embraces compounds of formula I wherein any one of $R_1$, $R_2$, and $R_3$ is methyl and the remaining groups are independently selected from $C_2$-$C_4$ alkyl; and all salts, stereoisomers, mixtures of stereoisomers, prodrugs, metabolites, solvates, and hydrates thereof. The $C_2$-$C_4$ alkyl groups are independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragments.

In another embodiment, the invention embraces compounds of formula I wherein any two of $R_1$, $R_2$, and $R_3$ are methyl and the remaining group is independently selected from $C_2$-$C_4$ alkyl; and all salts, stereoisomers, mixtures of stereoisomers, prodrugs, metabolites, solvates, and hydrates thereof. The $C_2$-$C_4$ alkyl group is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragment.

In another embodiment, the invention embraces compounds of formula I wherein $R_1$, $R_2$, and $R_3$ are all methyl, with the proviso that $R_{20}$ cannot be $C_6$ n-alkyl, $C_7$ n-alkyl, or $C_{11}$ n-alkyl. In an additional embodiment with this proviso, one and only one of $R_1$, $R_2$, and $R_3$ is methyl. In an additional embodiment with this proviso, two and only two of $R_1$, $R_2$, and $R_3$ are methyl. In an additional embodiment with this proviso, all three of $R_1$, $R_2$, and $R_3$ are methyl.

In another variation, in any of the embodiments of the compounds of formula I, alkenyl can include adjacent sites of unsaturation (e.g., allenyl, of the form —C=C=C—). In another variation, in any of the embodiments of the compounds of formula I, alkenyl excludes adjacent sites of unsaturation such as allenyl.

In other embodiments, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); Friedreich's Ataxia (FA); other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; other neurological diseases; epilepsy; genetic diseases; Huntington's Disease; mood disorders; schizophrenia; bipolar disorder; age-associated diseases; macular degeneration; diabetes; and cancer.

In another embodiment, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); and Friedreich's Ataxia (FA).

In another embodiment of the invention, including any of the foregoing embodiments, the mitochondrial disorder is Friedreich's ataxia (FRDA). In another embodiment of the invention, the mitochondrial disorder is Leber's Hereditary Optic Neuropathy (LHON). In another embodiment of the invention, the mitochondrial disorder is mitochondrial myopathy, encephalopathy, lactacidosis, stroke (MELAS). In another embodiment of the invention, the mitochondrial disorder is Kearns-Sayre Syndrome (KSS). In another embodiment of the invention, the mitochondrial disorder is Myoclonic Epilepsy with Ragged Red Fibers (MERRF). In another embodiment of the invention, the mitochondrial disorder is Parkinson's disease.

In another embodiment of the invention, including any of the foregoing embodiments, the compounds described herein are administered to subjects suffering from a mitochondrial disorder to modulate one or more of various energy biomarkers, including, but not limited to, lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2), and to modulate exercise intolerance (or conversely, modulate exercise tolerance) and to modulate anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In one embodiment, the levels are modulated to a value within about 2 standard deviations of the value in a healthy subject. In another embodiment, the levels are modulated to a value within about 1 standard deviation of the value in a healthy subject. In another embodiment, the levels in a subject are changed by at least about 10% above or below the level in the subject prior to modulation. In another embodiment, the levels are changed by at least about 20% above or below the level in the subject prior to modulation. In another embodiment, the levels are changed by at least about 30% above or below the level in the subject prior to modulation. In another embodiment, the levels are changed by at least about 40% above or below the level in the subject prior to modulation. In another embodiment, the levels are changed by at least about 50% above or below the level in the subject prior to modulation. In another embodiment, the levels are changed by at least about 75% above or below the level in the subject prior to modulation. In another embodiment, the levels are changed by at least about 100% above or at least about 90% below the level in the subject prior to modulation.

In another embodiment, including any of the foregoing embodiments, the subject or subjects in which a method of treating or suppressing a mitochondrial disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

In another embodiment, the invention embraces one or more compounds of formula I in combination with a pharmaceutically acceptable excipient, carrier, or vehicle.

In another embodiment, the invention embraces the use of one or more compounds of formula I in therapy. In another embodiment, the invention embraces the use of one or more compounds of formula I in the therapy of mitochondrial disease. In another embodiment, the invention embraces the use of one or more compounds of formula I in the manufacture of a medicament for use in therapy of mitochondrial disease.

For all of the compounds and methods described above, the quinone form can also be used in its reduced (hydroquinone) form when desired. Likewise, the hydroquinone form can also be used in its oxidized (quinone) form when desired. The phrase "compounds of formula (I)" is intended to include both the oxidized and reduced form of the compounds, unless otherwise specified.

MODES FOR CARRYING OUT THE INVENTION

The invention embraces compounds useful in treating or suppressing mitochondrial disorders, and methods of using such compounds for modulation of energy biomarkers. The redox active therapeutics for treatment or suppression of mitochondrial diseases and associated aspects of the invention are described in more detail herein.

By "subject," "individual," or "patient" is meant an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds disclosed herein and methods of the invention can then be administered to or practiced on asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein in addition to the non-salt compounds, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfinuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, can also be prepared.

The invention also includes all stereoisomers of the compounds, including diastereomers and enantiomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds which are themselves relatively inactive, but which convert into the active compound when introduced into the subject in which they are used, by a chemical or biological process in vivo, such as an enzymatic conversion. Suitable prodrug formulations include, but are not limited to, peptide conjugates of the compounds disclosed herein and esters of compounds disclosed herein. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The various compounds disclosed herein can be administered either as therapeutic agents in and of themselves, or as prodrugs which will convert to other therapeutically effective or effective substances in the body.

Metabolites of the compounds are also embraced by the invention. However, metabolites of substances which occur naturally in subjects are excluded from the claimed compounds of the invention.

"$C_1$-$C_4$ alkyl" is intended to embrace methyl (Me), ethyl (Et), propyl (Pr), n-propyl (nPr), isopropyl (iPr), butyl (Bu), n-butyl (nBu), isobutyl (iBu), sec-butyl (sBu), t-butyl (tBu), cyclopropyl (cyclPr), cyclobutyl (cyclBu), cyclopropyl-methyl (cyclPr-Me) and methyl-cyclopropane (Me-cyclPr), where the $C_1$-$C_4$ alkyl groups can be attached via any valence on the $C_1$-$C_4$ alkyl groups.

"Halogen" or "halo" substituents designates fluoro (—F), chloro (—Cl), bromo (—Br), and iodo (—I).

"$C_1$-$C_4$ haloalkyl" is intended to embrace any $C_1$-$C_4$ alkyl substituent having at least one halogen substituent; the halogen can be attached via any valence on the $C_1$-$C_4$ alkyl group. One subset of $C_1$-$C_4$ haloalkyl is —$CF_3$, —$CCl_3$, —$CBr_3$, and —$CI_3$. Another subset of $C_1$-$C_4$ haloalkyl is the subset with exactly one halogen substituent. Another subset of $C_1$-$C_4$ haloalkyl is the subset of $C_1$-$C_4$ perhaloalkyl; that is, $C_1$-$C_4$ alkyl with all available valences replaced by halogens. Another subset of $C_1$-$C_4$ haloalkyl is the subset of $C_1$-$C_4$ perfluoroalkyl; that is, $C_1$-$C_4$ alkyl with all available valences replaced by fluorines. Another subset of $C_1$-$C_4$ haloalkyl is the subset of $C_1$-$C_4$ perchloroalkyl; that is, $C_1$-$C_4$ alkyl with all available valences replaced by chlorines.

Synthesis of Compounds of Formula I

Synthesis of the compounds disclosed herein is readily accomplished by one of skill in the art. A synthesis of benzoquinone-type compounds is disclosed in U.S. Pat. No. 4,393, 075. Other methods of interest are found in U.S. Pat. No. 5,229,385 and U.S. Pat. No. 4,310,465.

A method of synthesizing compounds of formula I is by adapting the following synthesis for the compound (105):

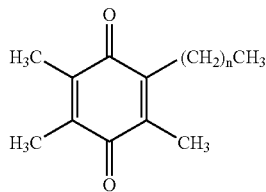

(105)

which is as follows:

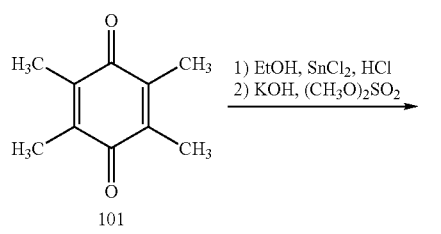

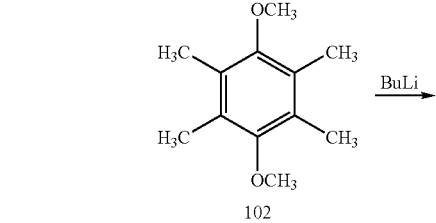

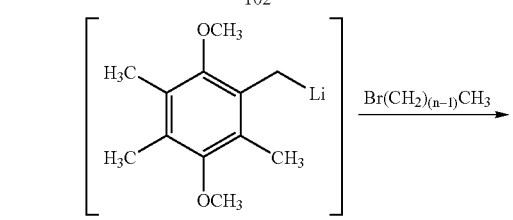

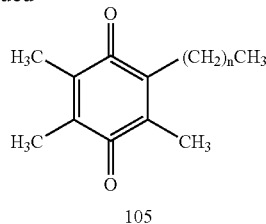

105 where the chemistry for conversion of duroquinone (101) into 3,6-dimethoxy-1,2,4,5-tetramethyl-1,4-cyclohexadiene (102) is described in Thomas et al., Journal of Organic Chemistry 51(22):4160 (1986); the chemistry for conversion of 3,6-dimethoxy-1,2,4,5-tetramethyl-1,4-cyclohexadiene (102) into the 3,6-dimethoxy-1-methylene lithium-2,4,5-trimethyl-1,4-cyclohexadiene (103) intermediate is described in Hübscher et al., Helvetica Chimica Acta 73(4):1068 (1990); and the chemistry for conversion of the 3,6-dimethoxy-1-alkyl-2,4,5-trimethyl-1,4-cyclohexadiene (104) into the 2-alkyl-3,5,6-trimethyl-1,4-benzoquinone (105) is described in Shiraishi et al., Journal of Medicinal Chemistry 32(9):2214 (1989). It should be noted that, while the reaction is illustrated with methyl as $R_1$, $R_2$, and $R_3$, other $R_1$, $R_2$, and $R_3$ substituents can be used at the methyl-substituted locations on the ring.

This synthesis can be easily modified to produce compounds with any combination of saturated, unsaturated and/or branched hydrocarbon chains by using the appropriate bromo compound, that is, by using a compound of the formula Br—$(CH_2)_3$—$R_{20}$ for the reaction converting 103 to 104, where $R_{20}$ is independently selected from —$C_1$-$C_{20}$ alkyl, —$C_1$-$C_{20}$ alkenyl, —$C_1$-$C_{20}$ alkynyl, and —$C_1$-$C_{20}$ containing at least one double bond and at least one triple bond.

Another method of making compounds of formula I is by adapting the following synthesis:

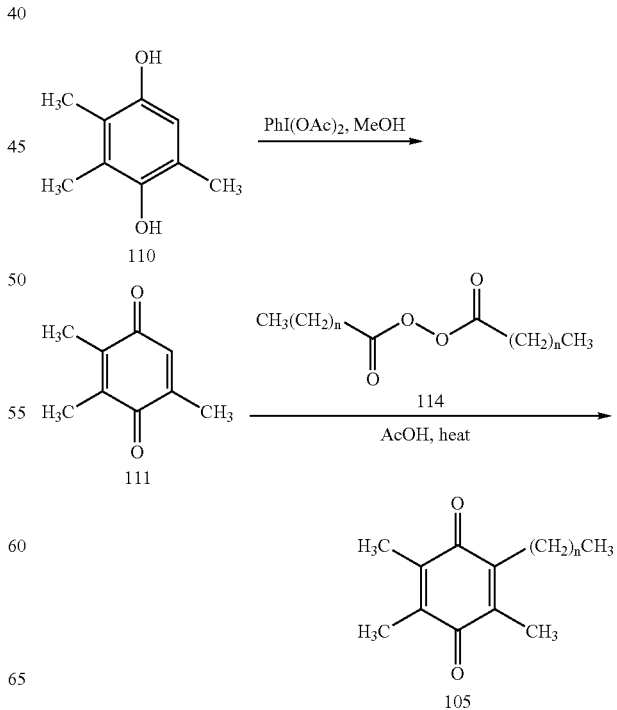

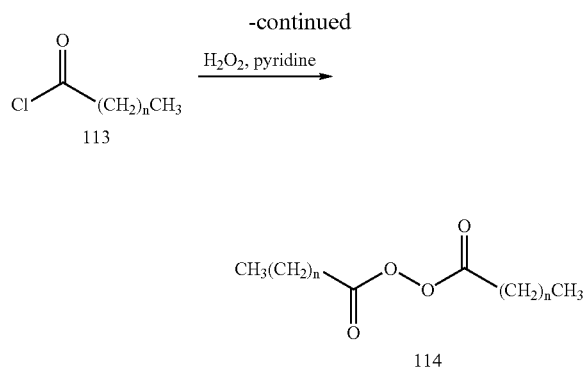

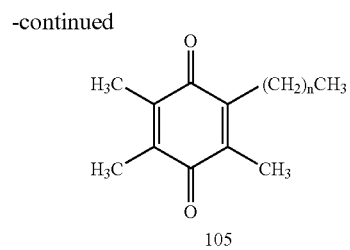

where the chemistry of converting 1,4-hydroxy-2,3,5-trimethylbenzene (110) into 2,3,5-trimethyl-1,4-benzoquinone (111) is described in Pelter et al., J. Chem. Soc., Perkin Trans. 1, (16), 1891 (1993), and the chemistry of converting the benzoquinone compound (111) into the 2-alkyl-3,5,6-trimethyl-1,4-benzoquinone (105) is described in Asin-Cayuela et al., FEBS Letters 571:9 (2004). As before, while the reaction is illustrated with methyl as $R_1$, $R_2$, and $R_3$, other $R_1$, $R_2$, and $R_3$ substituents can be used at the methyl-substituted locations on the ring.

Yet another method of making compounds of formula I uses chemistry adapted from Monte, W. T. and Lindbeck, A. C., Organic Process Research & Development 5:267-269 (2001), as follows. The $R_1$, $R_2$, $R_3$-substituted benzenediol is protected with methyl groups, and then a chloromethyl group is substituted for hydrogen at the valence on the benzene ring occupied by hydrogen.

where the chemistry of converting 1,4-hydroxy-2,3,5-trimethylbenzene (110) into 2,3,5-trimethyl-1,4-benzoquinone (111) is described in Pelter et al., J. Chem. Soc., Perkin Trans. 1, (16), 1891 (1993), the chemistry of converting the benzoquinone compound (111) into the 2-alkyl-3,5,6-trimethyl-1,4-benzoquinone (105) is described in Fieser et al., Journal of the American Chemical Society 64(9):2060 (1942), and the chemistry of converting the alkanoyl chloride (113) into the dialkanoyl peroxide (114) is described in Silbert et al., Journal of the American Chemical Society 81(10):2364 (1959). The following compound (115)

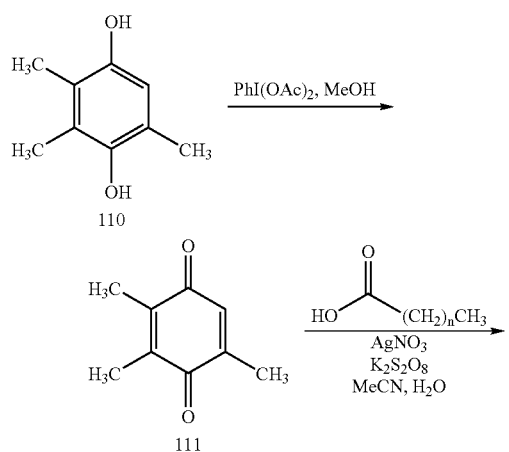

can be used to prepare compounds of formula I via this route, by starting with the appropriate 1,4-dihydroxy-2,3,5-substituted-1,4-benzoquinone and using the appropriate intermediate (115). Again, while the reaction is illustrated with methyl as $R_1$, $R_2$, and $R_3$, other $R_1$, $R_2$, and $R_3$ substituents can be used at the methyl-substituted locations on the ring.

Another method of making compounds of formula I is by the following decarboxylative coupling synthetic method:

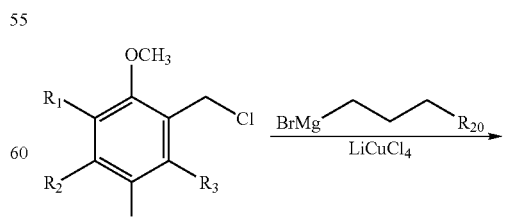

The chloromethyl compound is then reacted with a Grignard reagent of the form $R_{20}$—$(CH_2)_3$-MgX (where X is a Grignard-forming precursor, such as a halogen or metal that can be transmetallated with magnesium, such as lithium) to form the compound of formula I (reduced) with protected diols.

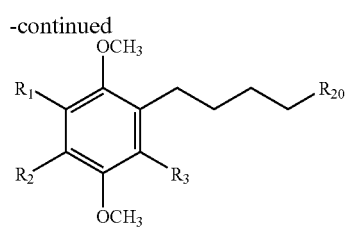

The product can be oxidized with concomitant removal of the methyl ethers to give quinone compounds of the formula I; that compound can be subsequently reduced with an appropriate reagent (such as sodium dithionite $Na_2S_2O_4$) to provide dihydroquinone compounds of formula I.

Interconvertibility of Quinone, Dihydroquinone Forms

The quinone and dihydroquinone forms of the compounds disclosed herein are readily interconverted with appropriate reagents. For example, the quinone form of a compound can be reduced to the dihydroquinone form with reducing agents such as sodium dithionite ($Na_2S_2O_4$). The hydroquinone form can be oxidized to the quinone form with oxidizing agents such as ceric ammonium nitrate or ferric chloride. The quinone and hydroquinone forms are also readily converted electrochemically, as is well known in the art. See, e.g., Section 33.4 of Streitweiser & Heathcock, Introduction to Organic Chemistry, New York: Macmillan, 1976.

Accordingly, the compounds of formula I can also be prepared in reduced form, that is, where the "head group" is a benzene-1,4-diol moiety instead of a 1,4-benzoquinone. These compounds are of the following formula I-Red:

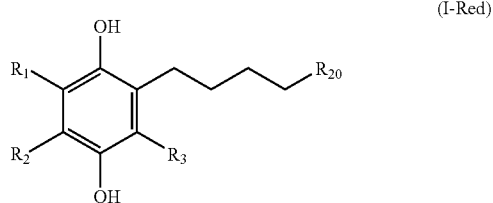

(I-Red)

where $R_1$, $R_2$, $R_3$, and $R_{20}$ are as described for formula I, and all salts, stereoisomers, solvates and hydrates thereof.

When the quinone form is drawn and followed by the phrase "reduced counterpart thereof" or "reduced form" or the like, the structure and the subsequent phrase are intended to embrace both the quinone and hydroquinone. Similarly, when the hydroquinone form is drawn and followed by the phrase "oxidized counterpart thereof" or "oxidized form thereof" or the like, the structure and the subsequent phrase are intended to embrace both the hydroquinone and quinone.

Diseases Amenable to Treatment or Suppression with Compounds Disclosed Herein, and Methods of the Invention A variety of diseases are believed to be caused or aggravated by mitochondrial disorders and impaired energy processing, and can be treated or suppressed using the compounds disclosed herein, and the methods of the invention. Such diseases include, but are not limited to, inherited mitochondrial diseases, such as Myoclonic Epilepsy with Ragged Red Fibers (MERRF), Mitochondrial Myopathy, Encephalopathy, Lactacidosis, Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), Friedreich's Ataxia (FA), other myopathies (including cardiomyopathy and encephalomyopathy), and renal tubular acidosis; neurodegenerative diseases, such as Parkinson's disease, Alzheimer's disease, amyotrophic lateral sclerosis (ALS, also known as Lou Gehrig's disease), motor neuron diseases; other neurological diseases such as epilepsy; genetic diseases such as Huntington's Disease (which is also a neurological disease); mood disorders such as schizophrenia and bipolar disorder; and certain age-associated diseases, particularly diseases for which CoQ10 has been proposed for treatment, such as macular degeneration, diabetes, and cancer.

Clinical Assessment of Mitochondrial Dysfunction and Efficacy of Therapy

Several readily measurable clinical markers are used to assess the metabolic state of patients with mitochondrial disorders. These markers can also be used as indicators of the efficacy of a given therapy, as the level of a marker is moved from the pathological value to the healthy value. These clinical markers include, but are not limited to, one or more of the previously discussed energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; anaerobic threshold; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, MELAS, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, MELAS, or KSS is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7): 695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4): 448-55 (1992)) and toxic mitochondrial myopathies (Chariot et al., Arthritis Rheum. 37(4):583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2): 287-91 (1997); Honda et al., Leuk. Res. 24(6):461-8 (2000); et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242 (7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al.,. Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al.,. Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of $NADH+H^+$, $NADPH+H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH ($NADH+H^+$) or NADPH ($NADPH+H^+$) can be measured by a variety of fluorescent, enzymatic, or electrochemical techniques, e.g., the electrochemical assay described in US 2005/0067303.

Oxygen consumption ($vO_2$ or VO2), carbon dioxide output ($VCO_2$ or VCO2), and respiratory quotient (VCO2/VO2): $vO_2$ is usually measured either while resting (resting $vO_2$) or at maximal exercise intensity ($vO_2$ max). Optimally, both values will be measured. However, for severely disabled patients, measurement of $vO_2$ max may be impractical. Measurement of both forms of $vO_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$)/(Cyt $C_{red}$), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds disclosed herein and the methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds disclosed herein and the methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds disclosed herein and the methods of the invention. RQ=respiratory quotient; BMR=basal metabolic rate; HR(CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomarker | Physical Effect |
|---|---|---|---|
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ $H^+$ gradient | Δ ATP | Organ dependent dysfunction |
| Respiratory Chain | ↓ Electron flux | Δ $VO_2$, RQ, BMR, ΔT, AT, pH | Metabolic dyscrasia & fatigue |
| Mitochondria & cytosol | ↓ ATP, ↓ $VO_2$ | Δ Work, ΔHR (CO) | Exercise intolerance |
| Mitochondria & cytosol | ↓ ATP | Δ PCr | Exercise intolerance |
| Respiratory Chain | ↓ Cyt $C_{Ox/Red}$ | Δ λ ~700-900 nM (Near Infrared Spectroscopy) | Exercise intolerance |
| Intermediary metabolism | ↓ Catabolism | Δ $C^{14}$-Labeled substrates | Metabolic dyscrasia & fatigue |
| Respiratory Chain | ↓ Electron flux | Δ Mixed Venous $VO_2$ | Metabolic dyscrasia & fatigue |
| Mitochondria & cytosol | ↑ Oxidative stress | Δ Tocopherol & Tocotrienols, CoQ10, docosahexaenoic acid | Uncertain |
| Mitochondria & cytosol | ↑ Oxidative stress | Δ $Glutathione_{red}$ | Uncertain |
| Mitochondria & cytosol | Nucleic acid oxidation | Δ8-hydroxy 2-deoxy guanosine | Uncertain |
| Mitochondria & cytosol | Lipid oxidation | ΔIsoprostane(s), eicosanoids | Uncertain |
| Cell membranes | Lipid oxidation | ΔEthane (breath) | Uncertain |
| Cell membranes | Lipid oxidation | ΔMalondialdehyde | Uncertain |

Treatment of a subject afflicted by a mitochondrial disease in accordance with the methods of the invention may result in the inducement of a reduction or alleviation of symptoms in the subject, e.g., to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one, or any combination of, the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of mitochondrial diseases, the compounds disclosed herein can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

When an increase in an energy biomarker level is desired to normalize the one or more such energy biomarker, the level of the energy biomarker can be increased to within about at least two standard deviations of normal in a subject, more preferably increased to within about at least one standard deviation of normal in a subject, increased to within about at least one-half standard deviation of normal, or increased to within about at least one-quarter standard deviation of normal, by administration of one or more compounds according to the invention. Alternatively, the level of one or more of the energy biomarkers can be increased by about at least 10% above the subject's level of the respective one or more energy biomarkers before administration, by about at least 20% above the subject's level of the respective one or more energy biomarkers before administration, by about at least 30% above the subject's level of the respective one or more energy biomarkers before administration, by about at least 40% above the subject's level of the respective one or more energy biomarkers before administration, by about at least 50% above the subject's level of the respective one or more energy biomarkers before administration, by about at least 75% above the subject's level of the respective one or more energy biomarkers before administration, or by about at least 100% above the subject's level of the respective one or more energy biomarkers before administration.

When a decrease in a level of one or more energy biomarkers is desired to normalize the one or more energy biomarkers, the level of the one or more energy biomarkers can be decreased to a level within about at least two standard deviations of normal in a subject, more preferably decreased to within about at least one standard deviation of normal in a subject, decreased to within about at least one-half standard deviation of normal, or decreased to within about at least one-quarter standard deviation of normal, by administration of one or more compounds according to the invention. Alternatively, the level of the one or more energy biomarkers can be decreased by about at least 10% below the subject's level of the respective one or more energy biomarkers before administration, by about at least 20% below the subject's level of the respective one or more energy biomarkers before administration, by about at least 30% below the subject's level of the respective one or more energy biomarkers before administration, by about at least 40% below the subject's level of the respective one or more energy biomarkers before administration, by about at least 50% below the subject's level of the respective one or more energy biomarkers before administration, by about at least 75% below the subject's level of the respective one or more energy biomarkers before administration, or by about at least 90% below the subject's level of the respective one or more energy biomarkers before administration.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a mitochondrial disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds disclosed herein can also be used in research applications. For example, a compound disclosed herein can be used for in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds disclosed herein can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds disclosed herein.

Additionally, the compounds can be used in biochemical tests or assays. Such tests can include incubation of one or more compounds disclosed herein with a tissue or cell sample from a subject to evaluate a subject's potential response (or the response of a specific subset of subjects) to administration of said one or more compounds, or to determine which compound produces the optimum effect in a specific subject or subset of subjects. One such test or assay would involve 1) obtaining a cell sample or tissue sample from a subject in which modulation of one or more energy biomarkers can be assayed; 2) administering one or more compounds disclosed herein to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds disclosed herein to the cell sample or tissue sample; 3) determining the amount of modulation of the one or more energy biomarkers after administration of the at least two compounds, compared to the status of the energy biomarker prior to administration of the at least compounds, and 4) selecting a compound for use in treatment, suppression, or modulation based on the amount of modulation determined in step 3).

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds disclosed herein may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions disclosed herein may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds disclosed herein may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds disclosed herein can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to one or more of the compounds disclosed herein, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N. W., p. 33 et seq (1976).

The invention also provides articles of manufacture and kits containing materials useful for treating or suppressing mitochondrial diseases. The article of manufacture comprises a container with a label. Suitable containers include, for example, bottles, vials, and test tubes. The containers may be formed from a variety of materials such as glass or plastic. The container holds a composition having an active agent which is effective for treating or suppressing mitochondrial diseases. The active agent in the composition is one or more of the compounds disclosed herein. The label on the container indicates that the composition is used for treating or suppressing mitochondrial diseases, and may also indicate directions for either in vivo or in vitro use, such as those described above.

The invention also provides kits comprising any one or more of the compounds disclosed herein. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy (or of the energy biomarker being modulated). The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds disclosed herein may be administered in a single daily dose, or the total daily dosage may be administered in divided dosage of two, three or four times daily.

While the compounds disclosed herein can be administered as the sole active pharmaceutical agent, they can also be used in combination with one or more other agents used in the treatment or suppression of disorders. Representative agents useful in combination with the compounds disclosed herein for the treatment or suppression of mitochondrial diseases include, but are not limited to, Coenzyme Q, vitamin E, idebenone, MitoQ, vitamins, and antioxidant compounds.

When additional active agents are used in combination with the compounds disclosed herein, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

The compounds disclosed herein and any other therapeutically active agents can be administered at the recommended maximum clinical dosage or at lower doses. Dosage levels of the active compounds in the compositions disclosed herein may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention is further illustrated by means of the following examples, which are not intended to limit the invention in any manner.

EXAMPLES

Example 1

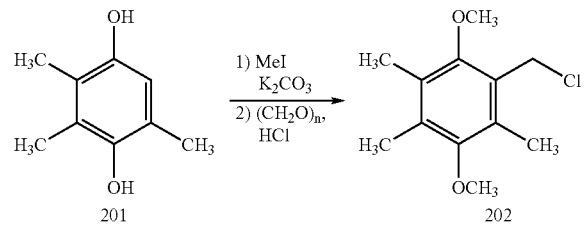

Step 1: A 2 L 3-N flask was charged with 2,3,5-trimethyl-benzene-1,4-diol (201; 50 g, 0.33 mol) and MEK (750 mL) to yield an amber solution. Potassium carbonate (210 g, 1.64 mol) was charged to the solution. After 30 min at room temperature, MeI (81.2 mL, 1.31 mol) was added to the brown suspension. The reaction mixture was heated to 65° C. for 72 h. After cooling to room temperature, the reaction mixture was concentrated to dryness by rotary evaporation to give a white paste. The paste was washed with EtOAc (3×300 mL). The EtOAc extracts were combined and concentrated by rotary evaporation. The resulting yellow-brown oil was chromatographed (80:20/heptanes:EtOAc) to yield 1,4-dimethoxy-2,3,5-trimethyl-benzene (47.2 g, 80%). $^1$H NMR (400 MHz; CDCl$_3$; ppm): 6.55 (s, 1H), 3.80 (s, 3H), 3.68 (s, 3H), 2.30 (s, 3H), 2.22 (s, 3H), 2.14 (s, 3H).

Step 2: A flask was charged with 1,4-dimethoxy-2,3,5-trimethyl-benzene (47.2 g, 0.26 mol), glacial acetic acid (250 mL), and paraformaldehyde (39.3 g, 1.31 mol) to yield a yellow suspension. Anhydrous HCl gas was then slowly bubbled through the reaction mixture for 1.5 h producing a clear amber solution. The reaction mixture was then diluted with water (300 mL) and extracted with MTBE (3×300 mL). The combined MTBE layers were dried over Na$_2$SO$_4$, filtered and concentrated by rotary evaporation. Purification of the crude product by silica gel chromatography (95:5/heptanes:EtOAc) yielded 1-chloromethyl-2,5-dimethoxy-3,4,6-trimethyl-benzene (202; 48.7 g, 81%). $^1$H NMR (400 MHz; CDCl$_3$; ppm): 4.76 (s, 2H), 3.81 (s, 3H), 3.68 (s, 3H), 2.36 (s, 3H), 2.23 (s, 3H), 2.21 (s, 3H).

Typical Procedure For Kochi Coupling: A 100 mL 3-N flask (A) was inerted and charged with 1-chloromethyl-2,5-dimethoxy-3,4,6-trimethyl-benzene (202; 3 g, 13.1 mmol) and degassed THF (30 mL). The flask was then cooled to 0° C. A separate 100 mL 3-N flask (B) was inerted and charged with the appropriate alkyl Grignard reagent (17.1 mmol). Flask B was then cooled to 0° C. A third 50 mL flask (C) was inerted and charged with copper (II) chloride (88 mg, 0.66 mmol), lithium chloride (56 mg, 1.32 mmol) and degassed THF (15 mL). After 5 min., the rusty orange solution in flask C was transferred to the solution of 1-chloromethyl-2,5-dimethoxy-3,4,6-trimethyl-benzene in flask A. The contents of flask A were then transferred dropwise via syringe to the Grignard solution in flask B over 30 min (exothermic). The reaction was allowed to stir for 16 h. The reaction was quenched with MTBE (20 mL) and saturated aqueous NH$_4$Cl (20 mL). After stirring for 10 min., the resulting suspension was filtered to remove dimerized side product. The aqueous layer was extracted with MTBE (3×20 mL). The combined MTBE layers were concentrated by rotary evaporation to yield a white residue. The residue was purified by silica gel chromatography (1:1/DCM:heptane) to yield desired coupled products (see 203, 204).

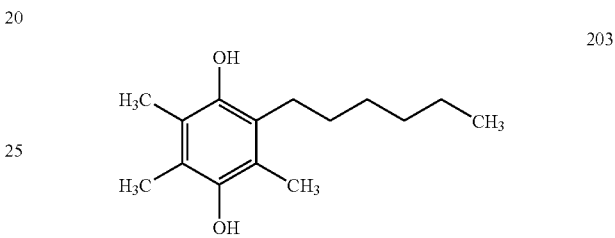

Using an n-pentyl Grignard reagent, 1-hexyl-2,5-dimethoxy-3,4,6-trimethyl-benzene (203) was synthesized (38%, clear colorless oil); $^1$H NMR (400 MHz; CDCl$_3$; ppm): 3.69 (s, 1H), 3.66 (s, 1H), 2.63-2.59 (m, 2H), 2.24 (s, 3H), 2.20 (s, 6 H), 1.53-1.28 (m, 8H), 0.90 (t, J=7.1 Hz, 3H).

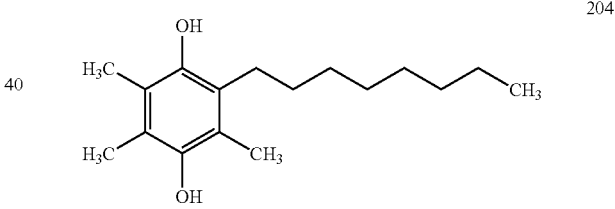

Using an n-heptyl Grignard reagent, 1-octyl-2,5-dimethoxy-3,4,6-trimethyl-benzene (204) was synthesized (57%, clear colorless oil); $^1$H NMR (400 MHz; CDCl$_3$; ppm): 3.71 (s, 1H), 3.68 (s, 1H), 2.65-2.61 (m, 2H), 2.25 (s, 3H), 2.21 (s, 6H), 1.53-1.31 (m, 12H), 0.92 (t, J=7.1 Hz, 3H).

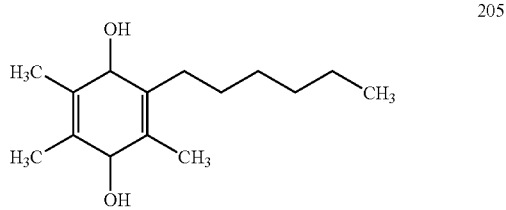

CAN Oxidation: A flask was charged with 1-hexyl-2,5-dimethoxy-3,4,6-trimethyl-benzene (203; 1.75 g, 7.5 mmol) and CAN (20 mL) then cooled to 0° C. A solution of CAN (8.4 g, 15.4 mmol) in water (10 mL) was added to the flask. After 1 h the reaction was complete. The reaction mixture was extracted with MTBE (3×20 mL). The combined MTBE layers were dried over MgSO₄, filtered and concentrated by rotary evaporation to yield 2-hexyl-3,5,6-trimethyl-[1,4]benzoquinone (205) as a yellow-orange oil which solidified upon standing (1.64 g, 88%). ¹H NMR (400 MHz; CDCl₃; ppm) 2.49-2.46 (m, 2H), 2.04 (s, 3H), 2.03 (s, 6H), 1.44-1.22 (m, 8H), 0.90 (t, J=7.1 Hz, 3H).

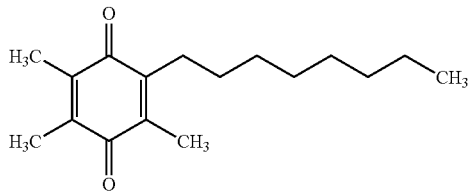

206 syringe pump. The reaction mixture was allowed to stir an additional 30 minutes at 70° C., then cooled to room temperature. To the mixture was added MTBE (200 ml) and water (100 ml). The organic layer was separated and washed with saturated NaHCO₃ (100 ml), then brine (2×200 ml). The MTBE solution was dried over sodium sulfate then concentrated to a yellow oil. The crude product, which contained residual unreacted starting quinone by TLC, was further purified by silica gel chromatography (120 g, 0-30% EtOAc:heptane) to give pure 2-heptadeca-8,11-dienyl-3,5,6-trimethyl-[1,4]benzoquinone (210; 0.474 g, 12.3%) as a yellow oil. ¹H NMR (400 MHz; d₆-DMSO; ppm): 5.36-5.26 (m, 4H), 2.73 (t, J=5.6 Hz, 2H), 2.42-2.38 (m, 2H), 2.02-1.93 (m, 4H). 1.95 (s, 3H), 1.93 (s, 6H). 1.34-1.22 (m, 16H), 0.84 (t, J=7.2 Hz, 3H).

Example 2B

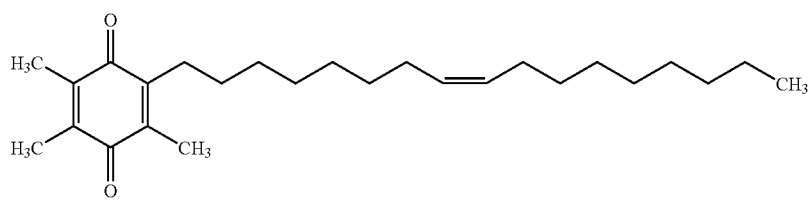

211

A flask was charged with 1-octyl-2,5-dimethoxy-3,4,6-trimethyl-benzene (204; 1.75 g, 7.5 mmol) and CAN (20 mL) then cooled to 0° C. A solution of CAN (8.4 g, 15.4 mmol) in water (10 mL) was added to the flask. After 1 h the reaction was complete. The reaction was diluted with water (50 mL) and the yellow precipitate was filtered and washed with water (20 mL). The fine yellow needles were dried under high vacuum to give pure 2-octyl-3,5,6-trimethyl-[1,4]benzoquinone (206; 1.69 g, 86%). ¹H NMR (400 MHz; CDCl₃; ppm): 2.49-2.45 (m, 2H), 2.04 (s, 3H), 2.03 (s, 6H), 1.45-1.19 (m, 12H), 0.89 (t,J=6.2 Hz, 3H).

Example 2

Decarboxylative Coupling

Example 2A

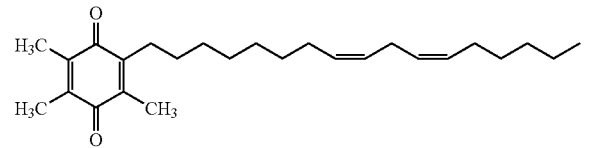

210

To a 250 ml round bottom flask was added 2,3,5-trimethyl-[1,4]benzoquinone (1.50 g, 9.98 mmole), linolenic acid (2.94 g, 10.4 mmole), and silver nitrate (1.83 g, 10.8 mmole) in a 1:1 mixture of water and acetonitrile (100 ml). The solution was heated to 70° C. under argon and an aqueous solution of K₂S₂O₈ (2.55 g, 11.5 mmole in 50 ml water) was added dropwise to the homogenous solution over 2.5 hours using a To a 250 ml round bottom flask was added 2,3,5-trimethyl-[1,4]benzoquinone (0.51 g, 3.4 mmole), oleic acid (1.0 g, 3.5 mmole), and silver nitrate (0.62 g, 3.6 mmole) in a 1:1 mixture of water and acetonitrile (100 ml). The solution was heated to 70° C. under argon and an aqueous solution of K₂S₂O₈ (0.86 g, 3.9 mmole in 50 ml water) was added dropwise to the homogenous mixture over 2.5 hours using a syringe pump. The reaction was stirred at 70° C. for an additional 30 minutes after addition, then cooled to room temperature. To the reaction mixture was added MTBE (200 ml) and water (100 ml). The organic layer was separated, washed with water (2×100 ml), then brine (2×100 ml). The solution was dried over sodium sulfate and concentrated to a yellow oil. The crude product was further purified by silica gel chromatography (120 g, 0-30% EtOAc:heptane) to give pure 2-heptadec-8-enyl-3,5,6-trimethyl-[1,4]benzoquinone (211; 25.2 mg, 2%) as a yellow oil. ¹H NMR (400 MHz; d₆-DMSO; ppm): 5.32-5.30 (m 2H), 2.42-2.38 (m, 2H), 1.98-1.93 (m, 4H), 1.95 (s, 3H), 193 (s, 6H), 1.40-1.22 (m, 22H), 0.84 (t, J=7.2 Hz, 3H).

Example 2C $$\underset{212}{\underset{\text{OH}}{\text{H}_3\text{C}}\text{—}\underset{\text{OH}}{\bigcirc}\text{—}\text{C(CH}_3)_3} \xrightarrow[\text{2) CAN}]{\text{1) (CH}_2\text{O)}_n, \text{SnCl}_2}$$

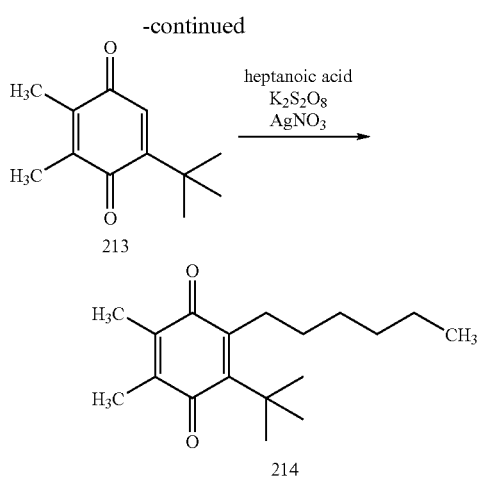

Step 1: To a 500 ml round bottom flask equipped with a stir-bar was added 2-tert-butyl-6-methyl-benzene-1,4-diol (212; 18 g, 100 mmole), paraformaldehyde (3.0 g, 100 mmole), SnCl$_2$ (47.4 g, 250 mmole), DME (200 ml), and concentrated HCl (50 ml, 35%). The flask was fitted with a reflux condenser and the reaction mixture was heated to 75° C. After 24 hours, the mixture was cooled to room temperature. To the mixture was added MTBE (300 ml). The organic fraction was separated and washed with water (3×500 ml) followed by brine (2×200 ml). The organic fraction was dried over sodium sulfate and concentrated to a red-brown foam. The resultant crude 5-tert-butyl-2,3-dimethyl-benzene-1,4-diol was taken directly to the next step with no further purification.

Step 2: To a 500 ml round bottom flask equipped with a stir-bar was added crude 5-tert-butyl-2,3-dimethyl-benzene-1,4-diol as a solution in MeCN (200 ml). To the stirring solution at room temperature was added CAN (114 g, 220 mmole) as a solution in water (200 ml) in one portion. The biphasic reaction mixture was stirred vigorously at room temperature for one hour, after which time no further reaction was detected by TLC analysis (20% EtOAc:heptane). The reaction mixture was poured into MTBE (500 ml). The organic layer was separated, then washed with water until the aqueous phase remained colorless (3×200 ml). The solution was then washed with brine (2×200 ml), dried over sodium sulfate, and concentrated to a red oil. A portion of the crude product was further purified by silica gel chromatography (120 g, 0-20% EtOAc:heptane) to give 5-tert-butyl-2,3-dimethyl-[1,4]benzoquinone (213) as a volatile yellow oil. $^1$H NMR (400 MHz; C$_6$D$_6$; ppm): 6.42 (s, 1H), 1.66 (q, J=1.2 Hz, 3H), 1.61 (q, J=1.2 Hz, 3H), 1.12 (s, 9H).

Step 3: To a 250 ml round bottom flask equipped with a stir-bar was added 5-tert-butyl-2,3-dimethyl-[1,4]benzoquinone (213; 0.68 g, 3.5 mmole), heptanoic acid (0.49 g, 3.7 mmole), AgNO$_3$ (0.64 g, 3.8 mmole), acetonitrile (50 ml) and water (50 ml). The fully homogenous solution was heated to 70° C. under argon while an aqueous solution of K$_2$S$_2$O$_8$ (0.91 g, 4.1 mmole in 30 ml water) was added dropwise over 2.5 hours using a syringe pump. The reaction mixture was allowed to stir an additional 30 minutes at 70° C., then cooled to room temperature. To the mixture was added heptane (100 ml) and water (100 ml). The organic layer was separated and washed with saturated NaHCO$_3$ (1×50 ml) followed by brine (2×100 ml). The organic layer was dried over sodium sulfate and concentrated to a yellow oil. The crude product was further purified by preparative TLC (silica gel: 200×200×2 mm; 100% heptane loading; 5% EtOAc:heptane elution). The fastest running bands, as visualized by UV, were excised, extracted from the silica gel with methyl tert-butyl ether, and the extract concentrated to a yellow oil to give a yellow oil. The residue was further purified by flash chromatography [silica gel: 40 g; 0-20% 100% heptane loading; 0-20% EtOAc/heptane gradient elution] to give pure 2-tert-butyl-3-hexyl-5,6-dimethyl-[1,4]benzoquinone (214; 83 mg, 8.4%) as a yellow oil. $^1$H NMR (400 MHz; C$_6$D$_6$; ppm): 2.71-2.67 (m, 2H), 1.67-1.66 (m, 6H), 1.51-1.24 (m, 8H), 1.37 (s, 9H), 0.88 (t, J=7.2 Hz, 3H).

Example 2D

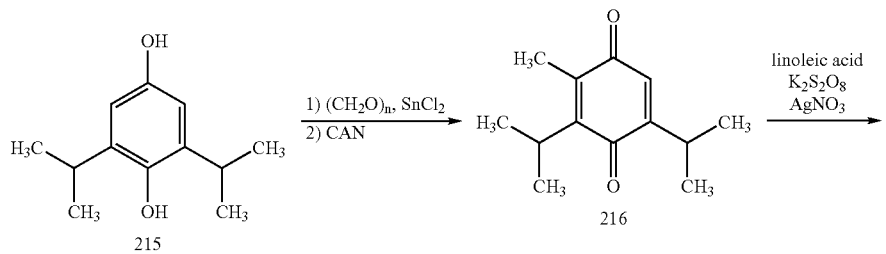

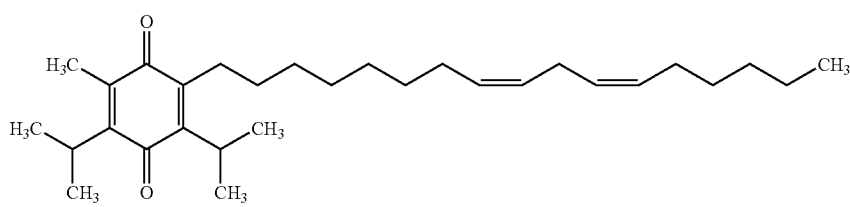

Step 1: To a 500 ml round bottom flask equipped with a stir-bar was added 2,6-diisopropyl-benzene-1,4-diol (215; 5.0 g, 26 mmole), paraformaldehyde (0.78 g, 26 mmole), $SnCl_2$ (18.9 g, 100 mmole), diisopropyl ether (200 ml), and concentrated HCl (60 ml, 35%). The flask was fitted with a reflux condenser and the reaction mixture was heated to 66° C. After 24 hours, the mixture was cooled to room temperature (the reaction remained biphasic throughout. To the reaction mixture was added MTBE (200 ml). The organic fraction was separated and washed with HCl solution (1×200 ml, 1N), water (3×100 ml), and brine (2×100 ml). The organic fraction was dried over sodium sulfate and concentrated to yellow oil. The resultant crude 2,6-diisopropyl-3-dimethyl-benzene-1,4-diol was taken directly to the next step with no further purification.

Step 2: To a 500 ml round bottom flask equipped with a stir-bar was added crude 2,6-diisopropyl-3-dimethyl-benzene-1,4-diol as a solution in MeCN (100 ml). To the stirring solution at room temperature was added CAN (28.5 g, 55.0 mmole) as a solution in water (100 ml) in one portion. The biphasic reaction mixture was stirred vigorously at room temperature for one hour, after which time no further reaction was detected by TLC analysis (20% EtOAc:heptane). The reaction mixture was poured into MTBE (200 ml). The organic layer was separated, then washed with water (2×100 ml). The solution was then washed with brine (2×100 ml), dried over sodium sulfate, and concentrated to a red-yellow oil. The crude product was further purified by silica gel chromatography (0-5% EtOAc:heptane) to give 3,5-diisopropyl-2-methyl-[1,4]benzoquinone (216) as a volatile yellow oil. $^1$H NMR (400 MHz; $C_6D_6$; ppm): 6.30 (d, J=1.4 Hz, 1H), 2.94-2.91 (m, 1H), 2.85-2.81 (m, 1H), 1.80 (d, J=1.2 Hz, 3H), 1.16 (d, J=6.8 Hz, 6H), 0.81 (dd, J=1.4 Hz, $J_2$=6.4 Hz, 6H).

Step 3: To a 250 ml round bottom flask equipped with a stir-bar was added 3,5-diisopropyl-2-methyl-[1,4]benzoquinone (216; 1.03 g, 5.00 mmol), linoleic acid (1.63 ml, 1.47 g, 5.24 mmol), silver(I) nitrate (917 mg, 5.40 mmol), acetonitrile (35 ml), and water (25 ml). The solution was heated under balloon-closed ambient atmosphere to 75° C., at which it was homogenous. Potassium persulfate (1.28 g, 5.75 mmol) in water (30 ml) was then added dropwise over 4 hours via syringe pump. Following complete addition the reaction mixture was heated for a further 2 hours and then the reaction volume reduced by approximately half under reduce pressure on a rotary evaporator. Water (50 ml) was added to the concentrate and the mixture extracted with MTBE (3×50 ml). The combined organics were washed with brine (50 ml), dried (sodium sulfate), and concentrated to a yellow oil. A portion of the crude product was further purified by preparative TLC (silica gel: 200×200×2 mm; 100% heptane loading; 5% MTBE:heptane elution). The fastest running bands, as visualized by UV, were excised, extracted from the silica gel with MTBE, and the extract concentrated to a yellow oil to give a yellow oil (280 mg). The residue was further purified by flash chromatography [silica gel: 40 g; 0-20% 100% heptane loading; 0-20% EtOAc/heptane gradient elution] to give 2-heptadeca-8,11-dienyl-3,5-diisopropyl-6-methyl-[1,4]benzoquinone (217; 65.6 mg, 2.9% mass yield) as a yellow oil which was pure as determined by reverse-phase HPLC. $^1$H NMR (400 MHz; $d_6$-DMSO; ppm): 5.40 (m, 4H), 3.05-2.94 (m, 2H), 2.73 (t, J=5.6 Hz, 2H), 2.47-2.30 (m, 2H), 2.02-196 (m, 4H), 1.95 (s, 3H), 1.29-1.20 (m, 16H), 1.21 (d, J=6.8 Hz, 6H), 1.19 (d, J=7.2 Hz, 6H), 0.84 (t, J=7.2 Hz, 3H).

Example 2E

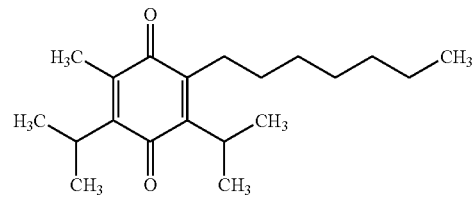

218

To a 100 ml round bottom flask equipped with a stir-bar was added 3,5-diisopropyl-2-methyl-[1,4]benzoquinone (216, see Example 2D; 1.03 g, 5.00 mmol), octanoic acid (83211, 757 mg, 5.24 mmole), silver (I) nitrate (917 mg, 5.40 mmol), acetonitrile (35 ml), and water (25 ml). The solution was heated under balloon-closed ambient atmosphere to 75° C. and was homogenous. Potassium persulfate (1.28 g, 5.75 mmol) in water (30 ml) was then added dropwise over 4 hours via syringe pump. Following complete addition the reaction mixture was heated for a further 2 hours and then the reaction volume reduced by approximately half under reduce pressure on a rotary evaporator. Water (50 ml) was added to the concentrate and the mixture extracted with MTBE (3×50 ml). The combined organics were washed with brine (50 ml), dried (sodium sulfate), and concentrated to a yellow oil (1.2 g). Approx. 75% of the residue was purified in 150-200 mg portions by preparative-TLC [silica gel: 200×200×2 mm; 100% heptane loading; 5% ethyl acetate/heptane elution]. The fastest running bands, as visualized by UV, were combined, extracted from the silica gel with MTBE, and the extract concentrated to a yellow oil (~300 mg). The residue was further purified by flash chromatography [silica gel: 120 g; 100% heptane loading; 3-6% ethyl acetate/heptane gradient elution] to give the 2-heptyl-3,5-diisopropyl-6-methyl-[1,4]benzoquinone (218) as a bright yellow oil (288 mg, 21% mass yield). $^1$H NMR (400 MHz; $C_6D_6$; ppm): 2.93-2.80 (m, 2H), 2.49-2.46 (m, 2H), 1.84 (s, 3H), 1.43-1.18 (m, 10H), 1.33 (d, J=6.8 Hz, 6H), 1.19 (d, J=6.8 Hz, 6H), 0.88 (t, J=7.2 Hz, 3H).

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating a mitochondrial disorder, modulating one or more energy biomarkers, normalizing one or more energy biomarkers, or enhancing one or more energy biomarkers, comprising administering to a subject a therapeutically effective amount or effective amount of one or more compounds of the formulas:

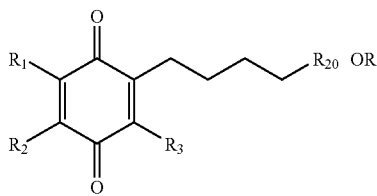

(I)

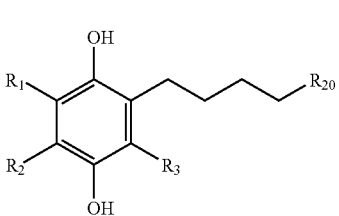

(I-RED)

where $R_1$ and $R_2$ are independently selected from —$C_1$-$C_4$ alkyl, —$C_1$-$C_4$ haloalkyl, —CN, —F, —Cl, —Br, and —I;

$R_3$ is selected from —$C_1$-$C_4$ alkyl, —$C_1$-$C_4$ haloalkyl, —CN, —F, —Cl, and —I;

$R_{20}$ is independently selected from —$C_1$-$C_{20}$ alkyl, —$C_1$-$C_{20}$ alkenyl, —$C_1$-$C_{20}$ alkynyl, and —$C_1$-$C_{20}$ containing at least one double bond and at least one triple bond;

and all salts, stereoisomers, mixtures of stereoisomers, and prodrugs thereof.

2. The method of claim 1, with the proviso that $R_{20}$ excludes $C_6$ n-alkyl, $C_7$ n-alkyl, and $C_{11}$ n-alkyl.

3. The method of claim 1, where $R_1$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment;

where $R_2$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment;

where $R_3$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment;

where $R_{20}$ is independently selected from —$C_1$-$C_{20}$ alkyl, —$C_1$-$C_{20}$ alkenyl, —$C_1$-$C_{20}$ alkynyl, and —$C_1$-$C_{20}$ containing at least one double bond and at least one triple bond and all salts, stereoisomers, mixtures of stereoisomers, and prodrugs thereof.

4. The method of claim 3, with the proviso that $R_{20}$ excludes $C_6$ n-alkyl, $C_7$ n-alkyl, and $C_{11}$ n-alkyl.

5. The method of claim 1, wherein at least one of $R_1$, $R_2$, and $R_3$ is not methyl.

6. The method of claim 2, wherein at least one of $R_1$, $R_2$, and $R_3$ is not methyl.

7. The method of claim 3, wherein at least one of $R_1$, $R_2$, and $R_3$ is not methyl.

8. The method of claim 4, wherein at least one of $R_1$, $R_2$, and $R_3$ is not methyl.

9. The method of claim 1, wherein the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); Friedreich's Ataxia (FA); other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; epilepsy; Huntington's Disease; mood disorders; schizophrenia; bipolar disorder; macular degeneration; diabetes; and lung cancer.

10. The method of claim 1, wherein the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); and Friedreich's Ataxia (FA).

11. The method of claim 1, wherein the energy biomarker is selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+$H^+$) levels; NADPH (NADPH+$H^+$) levels; NAD levels; NADP levels; ATP levels; reduced coenzyme Q ($CoQ^{red}$) levels; oxidized coenzyme Q ($CoQ^{ox}$) levels; total coenzyme Q ($CoQ^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; levels of oxygen consumption (VO2); levels of carbon dioxide output (VCO2); respiratory quotient (VCO2/VO2); exercise tolerance; and anaerobic threshold.

12. The method of claim 1, wherein the subject is selected from the group consisting of: a subject with a mitochondrial disease; a subject undergoing strenuous or prolonged physical activity; a subject with chronic energy problems; a subject with chronic respiratory problems; a pregnant female; a pregnant female in labor; a neonate; a premature neonate; a subject exposed to an extreme environment; a subject exposed to a hot environment; a subject exposed to a cold environment; a subject exposed to an environment with lower-than-average oxygen content; a subject exposed to an environment with higher-than-average carbon dioxide content; a subject exposed to an environment with higher-than-average levels of air pollution; a subject with lung disease; a subject with lower-than-average lung capacity; a tubercular patient; a lung cancer patient; an emphysema patient; a cystic fibrosis patient; a subject undergoing acute trauma; a subject in shock; a subject requiring acute oxygen administration; a subject requiring chronic oxygen administration; an elderly subject; an elderly subject experiencing decreased energy; and a subject suffering from chronic fatigue.

13. A compound of the formula:

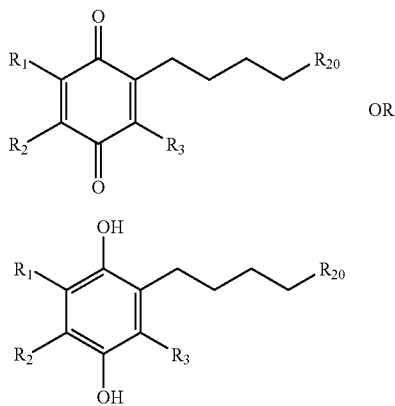

where $R_1$ is selected from —$C_1$-$C_4$ alkyl, —$C_1$-$C_4$ perhaloalkyl, —CN, —F, -and —Br;

$R_2$ is selected from —$C_1$-$C_4$ alkyl, —$C_1$-$C_4$ perhaloalkyl, —CN, —F, —Cl,—Br, and —I;

$R_3$ is selected from —$C_1$-$C_4$ alkyl, —$C_1$-$C_4$ perhaloalkyl, —CN, —F, —Cl, and —I;

$R_{20}$ is independently selected from —$C_1$-$C_{20}$ alkyl, —$C_1$-$C_{20}$ alkenyl, —$C_1$-$C_{20}$ alkynyl, and —$C_1$-$C_{20}$ containing at least one double bond and at least one triple bond;

with the proviso that $R_{20}$ excludes $C_6$ n-alkyl, $C_7$ n-alkyl, and $C_{11}$ n-alkyl when $R_1$, $R_2$, and $R_3$ are all methyl; and all salts, stereoisomers, mixtures, of stereosoisomers, and prodrugs thereof.

14. A compound of claim 13, where $R_{20}$ excludes $C_6$ n-alkyl, $C_7$ n-alkyl, and $C_{11}$ n-alkyl for any selections of $R_1$, $R_2$, and $R_3$.

15. A compound of claim 13, where $R_1$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment;

where $R_2$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment;

and where $R_3$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment;

and all salts, stereoisomers, mixtures of stereoisomers, and prodrugs thereof.

16. A compound of claim 13, wherein at least one of $R_1$, $R_2$, and $R_3$ is not methyl, and all salts, stereoisomers, mixtures of stereoisomers, and prodrugs thereof.

17. A compound of claim 16, wherein $R_1$, $R_2$, and $R_3$ are independently selected from $C_2$-$C_4$ alkyl, and all salts, stereoisomers, mixtures of stereoisomers, and prodrugs thereof.

18. A compound of claim 13, wherein one and only one of $R_1$, $R_2$, and $R_3$ is methyl, and all salts, stereoisomers, mixtures of stereoisomers, and prodrugs thereof.

19. A compound of claim 13, wherein two and only two of $R_1$, $R_2$, and $R_3$ are methyl, and all salts, stereoisomers, mixtures of stereoisomers, and prodrugs thereof.

20. A compound of claim 13, wherein all of $R_1$, $R_2$, and $R_3$ are methyl, and all salts, stereoisomers, mixtures of stereoisomers, and prodrugs thereof.

21. A pharmaceutical composition comprising a compound of claim 13 and a pharmaceutically acceptable carrier.

\* \* \* \* \*

UNITED STATES PATENT AND TRADEMARK OFFICE
CERTIFICATE OF CORRECTION

| | |
|---|---|
| PATENT NO. | : 7,432,305 B2 |
| APPLICATION NO. | : 11/521887 |
| DATED | : October 7, 2008 |
| INVENTOR(S) | : Guy M. Miller et al. |

Page 1 of 1

It is certified that error appears in the above-identified patent and that said Letters Patent is hereby corrected as shown below:

In column 37, line 32, please replace "mixtures, of stereosoisomers," with --mixtures of stereoisomers,--.

Signed and Sealed this

Second Day of December, 2008

JON W. DUDAS
*Director of the United States Patent and Trademark Office*